(12) United States Patent
You et al.

(10) Patent No.: US 6,995,137 B2
(45) Date of Patent: Feb. 7, 2006

(54) WATER-SOLUBLE NATURAL FILM AND ITS PREPARING METHOD

(75) Inventors: Hyung Ja You, Seongnam-si (KR); Sang Bong Seo, Seongnam-si (KR)

(73) Assignee: Jakwang Co., Ltd., Gyeonggi-do (KR)

( * ) Notice: Subject to any disclaimer, the term of this patent is extended or adjusted under 35 U.S.C. 154(b) by 97 days.

(21) Appl. No.: 10/730,920

(22) Filed: Dec. 10, 2003

(65) Prior Publication Data
US 2004/0137041 A1    Jul. 15, 2004

(30) Foreign Application Priority Data
Jan. 9, 2003    (KR) .................... 10-2003-0001286

(51) Int. Cl.
*A61K 38/16* (2006.01)
*A61K 31/70* (2006.01)
(52) U.S. Cl. ............................... 514/8; 514/2; 514/55
(58) Field of Classification Search .................. 514/2, 514/8, 55
See application file for complete search history.

(56) References Cited

U.S. PATENT DOCUMENTS

| 3,533,940 | A | 10/1970 | Peniston et al. |
| 4,699,135 | A | 10/1987 | Motosugi et al. |
| 4,996,307 | A | 2/1991 | Itoi et al. |
| 5,900,479 | A | 5/1999 | Glasser et al. |
| 6,747,015 | B2 * | 6/2004 | Byon et al. .................... 514/54 |

FOREIGN PATENT DOCUMENTS

KR    2003-0005593    1/2003

OTHER PUBLICATIONS

Seo et al.; "Preparation of Multifunctional Low Molecular Weight Chitosan and its Application in Cosmetics"; International Federation of the societies of Cosmetic Chemists Proceedings of the 20th IFSCC Congress: Cannes, France Sep. 14-18, 1998; SOFW-Journal, 128, pp. 34-37, (2002).
Seo et al.; Development of a Natural Preservative System Using the Mixture of Chitosan-*INULA* Helenium L. Extract; International Journal of Cosmetic Science, vol. 24, pp. 195-206, (2002).

* cited by examiner

*Primary Examiner*—Elli Peselev
(74) *Attorney, Agent, or Firm*—Finnegan, Henderson, Farabow, Garrett & Dunner, LLP

(57) ABSTRACT

The present invention relates to water-soluble natural film and its preparing method. More particularly, the present invention relates to water-soluble natural film manufactured by dissolving as an active ingredient a water-soluble chitosan prepared in such a manner that chitin/chitosan decomposed with lysozyme is rinsed with ethanol, subjected to electric adjustment and sonication in a saline solution and to ion-exchange to obtain water-soluble $\beta$-glucosamine fibrin followed by nano-sized coating the $\beta$-glucosamine fibrin with immunoglobulin ($\gamma$-globulin), and seaweeds and functional ingredients in distilled water and gelatinating. The water-soluble natural film according to the present invention, unlike the conventional film containing chitosan, comprises, at a predetermined content ratio, chitosan with improved water solubility and immunity, seaweeds and functional ingredients. Therefore, it imparts elasticity to matrix of a film to enable film molding with convenience and renders more compatibility to human body due to natural materials as its active ingredients, eliciting more favorable feeling when taken in. In particular, the film composition itself is processed to form a film with a desired thickness and size or is coated on a conventional biodegradable resin film, being applicable to a film in preparing an oral cleaning agent with immediate effect and a food packaging material.

5 Claims, 2 Drawing Sheets

WATER-SOLUBLE NATURAL FILM AND ITS PREPARING METHOD

BACKGROUND OF THE INVENTION

1. Field of the Invention

The present invention relates to water-soluble natural film and its preparing method. More particularly, the present invention relates to water-soluble natural film manufactured by dissolving as an active ingredient a water-soluble chitosan prepared in such a manner that chitin/chitosan decomposed with lysozyme is rinsed with ethanol, subjected to electric adjustment and sonication in a saline solution and to ion-exchange to obtain water-soluble β-glucosamine fibrin followed by nano-sized coating the β-glucosamine fibrin with immunoglobulin (γ-globulin), and seaweeds and functional ingredients in distilled water and gelatinating.

2. Description of the Related Art

Chitosan is an aminopolysaccharide present in nature, which is typically obtained by deacetylation of chitin found in shells of crab and shrimp, cuttlebones, and cell walls of fungi, mushrooms and bacteria. Chitosan exhibits nontoxic, biodegradable and biocompatible. In addition, chitosan is useful in tissue culture and has antibiotic activity and hemostatic activity. Furthermore, chitosan has been known to show a variety of physiological functions such as reduction of cholesterol level, promotion of metabolism in intestine, anticancer activity via enhancing immunity, improvement of liver function, reduction of glucose level in blood and detoxification of heavy metals.

Chitin exhibits strong resistance to chemical reagents and insolubility in water and organic solvents via strong intramolecular hydrogen bonds due to the presence of acetylamino groups in the molecule. Such properties make it difficult to process chitin for the formation fiber and film and therefore act as an obstacle against active application of chitin. Therefore, various attempts have been made to obtain water-soluble chitosan with excellent physical properties compared to chitin. Chitin has been typically converted via its deacetylation to chitosan that exhibits water solubility in aqueous phase with weak acidity.

Chitin and chitosan have been primarily used as a flocculant for recovering active ingredients in waste water generated by food plants. Recently, they have been improved by modification and thus extended their applications to a wide variety of fields including food, medicines, functional membranes, biotechnology, cosmetics, agriculture, chemical engineering and environment. Meanwhile, a high quality and functional chitin or chitosan useful in clinical medicine widens its fields of application; however, the conventional methods developed so far fail to meet the requirements for preparing chitin or chitosan that exhibits higher functionality and applicability to various clinical medicines.

Various techniques have been proposed to process chitin or chitosan for the formation of film or fiber:

U.S. Pat. No. 3,533,940 discloses that chitosan prepared from chitin is dissolved in aqueous organic acid solution such acid acetic acid to form a solution for forming fiber or film. In addition, U.S. Pat. No. 4,699,135 teaches (a) a method for preparing chitin fiber performed by dissolving chitin in a polar organic solvent such as dimethylacetamide containing lithium chloride and (b) a chitosan monofiber obtained from chitosan dissolved in an aqueous solution of acetic acid.

U.S. Pat. No. 4,996,307 discloses a method for preparing water-soluble acylated chitosan with high molecular weight having a degree of acylation of 35–65, in which the acylated chitosan may be obtained in high yield within a few hours in the same system. Further, U.S. Pat. No. 5,900,479 discloses a method for preparing water-insoluble chitinous film or fiber by use of a chitosan solution that is obtained by dissolving chitin in an aqueous organic acid solution.

However, the final products made of the films and fibers prepared by the methods described above are solution containing organic acid or have dissolved form in organic acid, so that the films and fibers with no water solubility show limited applicability.

SUMMARY OF THE INVENTION

The present inventors have intensive researches to overcome the problems associated with water-insolubility, and as a result, it has been found that water-soluble natural film manufactured by incorporating as an active ingredient a water-soluble chitosan prepared in such a manner that chitin/chitosan decomposed with lysozyme is rinsed with ethanol, subjected to electric adjustment and sonication in a saline solution and to ion-exchange to obtain water-soluble β-glucosamine fibrin followed by nano-sized coating the β-glucosamine fibrin with immunoglobulin (γ-globulin), and seaweeds and functional ingredients that may impart elasticity to film matrix, which permits to form film conveniently, has exhibited excellent compatibility to human body due to natural materials as its active ingredients, eliciting more favorable feeling when taken in.

In addition, the present inventors have discovered to overcome the shortcomings described above, where the raw materials including chitosan described above dissolved in water are cured to obtain the material with certain viscosity for film formation and is then subjected to compression-molding, or is sprayed stepwise on hydrophobic or biodegradable conventional film, followed by solidifying in a mixed crystallization solution containing ethanol of 95–99.9 wt % and glutaraldehyde of 0.1–5 wt %. Consequently, based on the findings described above, the present invention has been completed.

Accordingly, the object of this invention is to provide water-soluble natural film containing chitosan exhibiting functional properties and its preparing method.

DETAILED DESCRIPTION OF THIS INVENTION

Figure 1:
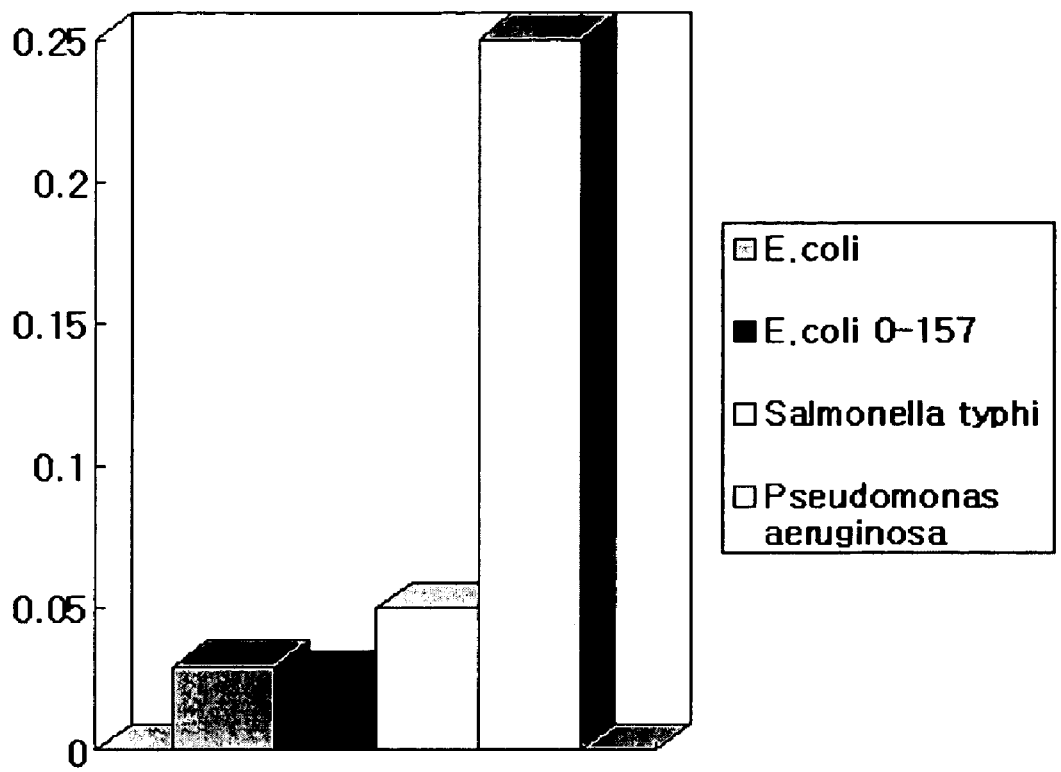
FIG. 1 is a graph showing the measurement results of minimum inhibitory concentration against gram-negative bacteria of chitosan used in the present natural film.

In an aspect of the present invention, there is provided water-soluble natural film composition containing chitosan, which comprises: (a) 20–99.98 wt % of water-soluble chitosan with enhanced immunity prepared in such a manner that chitin/chitosan decomposed with lysozyme is sonicated in a saline solution and is subjected to ion-exchange to obtain water-soluble β-glucosamine fibrin followed by nanocoating the β-glucosamine fibrin with γ-globulin as an immune protein; (b) 0.01–75 wt % of at least one seaweeds selected from the group consisting of *Gelidium amansii*, jellyfish, brown seaweed, tangle and their extracts; and (c) 0.01–30 wt % of at least one functional ingredients selected from the group consisting of γ-globulin, cholic acid, astaxanthin, rutin, lecithin, *Inula helenium* L., cellulose and collagen.

In another aspect of the present invention, there is provided a method for preparing water-soluble natural film containing chitosan, which comprises the steps of: (a) preparing water-soluble chitosan with enhanced immunity prepared in such a manner that chitin/chitosan decomposed with lysozyme is sonicated in a saline solution and is subjected to ion-exchange to obtain water-soluble β-glucosamine fibrin followed by nanocoating said β-glucosamine fibrin with γ-globulin as an immune protein; (b) preparing a gel with a concentration of 0.001 to 70% by dissolving in distilled water 20–99.98 wt % of said water-soluble chitosan with enhanced immunity; 0.01–75 wt % of at least one seaweeds selected from the group consisting of *Gelidium amansii*, jellyfish, brown seaweed, tangle and their extracts; and 0.01–30 wt % of at least one functional ingredients selected from the group consisting of γ-globulin, cholic acid, astaxanthin, rutin, lecithin, *Inula helenium* L., cellulose and collagen; (c) curing said gel prepared in the step of (b), whereby said gel shows a viscosity of 10 to 150 cps; (d) hardening said gel cured in the step of (c) with ethanol of 95–99.9 wt % and glutaraldehyde of 0.1–5 wt %; and (e) compression-molding said hardened gel in the step of (d) or spraying said hardened gel on one side or both sides of biodegradable film or conventional film, followed by drying.

The present invention will be described in more detail as follow:

The present invention is directed to water-soluble natural film and its preparing method. More particularly, the present invention is directed to water-soluble natural film comprising as an active ingredient a water-soluble chitosan prepared in such a manner that chitin/chitosan decomposed with lysozyme is rinsed with ethanol, sonicated in a saline solution and is subjected to ion-exchange to obtain water-soluble β-glucosamine fibrin followed by nano-sized coating the β-glucosamine fibrin with immunoglobulin (γ-globulin), and seaweeds and functional ingredients. The three ingredients are gelatinated to give water-soluble natural film of interest. Compared to the conventional film containing chitosan, the water-soluble natural film of the present invention exhibit higher water solubility, so that the antibiotic activity of water-soluble chitosan is applicable to more various fields, and seaweeds and functional ingredients contained impart elasticity to matrix of a film to enable film molding with convenience. In addition, since the natural film of this invention comprise natural materials as active ingredients, it shows more compatibility to human body and elicits more favorable feeling when taken in. In addition to this, the natural film of this invention manufactured by molding a composition as film with desired thickness and size, is easy to carry and take in, so that it is very suitable in a film as an oral cleaning agent with immediate effect. Where the natural film of this invention manufactured by coating conventional biodegradable film is applied to a packaging material, it is successful in preventing the growth of harmful microorganisms responsible for putrefaction of food owing to its excellent antibiotic activity, so that it is possible to freshly store food in a long period of time. Additionally, owing to its good biodegradability, the film is used as natural-degradable packaging material.

The water-soluble chitosan used in this invention can be prepared in such a manner that chitin/chitosan as a naturally-occurring biomacromolecule substance is decomposed with lysozyme, subjected to rinsing with ethanol, electric adjustment and sonication in a saline solution, and ion-exchange to obtain water-soluble β-glucosamine fibrin followed by nano-sized coating with immunoglobulin (γ-globulin) (see Korean Pat. Appln. No. 2001-40955). Therefore, it could be recognized that the water-soluble chitosan with enhanced immunity is distinct from the conventional chitosan in the sense that it comprises functional elements.

The water-soluble chitosan used in this invention generally has a molecular weight of 1,000–1,000,000 Da, preferably, 100,000–500,000 Da. The chitosan having molecular weight of 100,000–500,000 Da permits to provide a film with improved antibiotic activity and physical properties. The research results on the antibiotic activity of the chitosan having molecular weight of 100,000–500,000 Da was reported in 1998 at International federation of the societies of cosmetic chemists proceedings held on Cannes France (International federation of the societies of cosmetic chemists proceedings of the 20th IFSCC Congress: Cannes France Sep. 14–18, 1998 "Preparation of multi functional low molecular weight chitosan and its application in cosmetics", Discover the secret of asian natural beauty (5th ASCS 2001):1–3 March, Bangkok, Thailand. "development of natural preservative system using the mixture of chitosan-*Inula Helenium* L. extracts").

The water-soluble chitosan with enhanced immunity used in this invention has a molecular weight range of 100,000–500,000 Da and shows a high viscosity ranging from 10 to 150 cps (Brookfield viscometer). Where the molecular weight fails to fall under the range, the high antibiotic activity against bacteria associated with oral cavity and food may be negligible; and where the viscosity fails to fall under the range, the molding process to form film is difficult.

The natural film of this invention comprises 20–99.98 wt % of the water-soluble chitosan with enhanced immunity having characteristics described above, together with 0.01–75 wt % of seaweeds and 0.01–30 wt % of functional ingredient as matrix constituents.

The seaweeds may be at least one selected from the group consisting of *Gelidium amansii*, jellyfish, brown seaweed, tangle and their extracts. Since the seaweeds are naturally occurring material compatible to human body, they are helpful in human body when taken in. In addition, the mucous constituent of the seaweeds may alleviate more or less harsh character of chitosan when taken in, to elicit soft feeling in oral cavity, and may impart viscosity and elasticity when molding to film, so that the formation of matrix becomes more convenient. The water-soluble natural film composition containing chitosan comprises 0.01–75 wt % of the seaweed. If the amount is less than 0.01 wt %, the properties described above does not exhibited; and if the amount is more than 75 wt %, the amount of water-soluble chitosan with enhanced immunity is relatively decreased, so that the high antibiotic activity cannot be anticipated.

Besides seaweeds, as a constituent, the functional ingredient may be at least one albuminoid selected from the group consisting of γ-globulin, cholic acid, astaxanthin, rutin, lecithin, *Inula helenium* L., cellulose and collagen. Similar to seaweeds, the natural-occurring functional ingredient contained the water-soluble natural film composition imparts various functions to the film and shows high compatibility to human body. In addition, it is very miscible with the water-soluble chitosan with enhanced immunity, so that the synergic effect may be anticipated, and the formation of matrix when film formation becomes more convenient. The water-soluble natural film composition comprises 0.01–30 wt % of the functional ingredient. If the amount is less than 0.01 wt %, the properties described above are not exhibited; and if exceeding 30 wt %, there may arise a problem in the formation of a film.

Different from the conventional chitosan-containing film, the water-soluble natural film containing chitosan of this invention employs as a raw material water-soluble chitosan having high molecular weight with enhanced immunity and antibiotic activity, and exhibits excellent water solubility.

That is, the water-soluble chitosan in this invention, prepared in such a manner that a chitin/chitosan as natural-occurring biomacromolecule substance is decomposed with lysozyme, is subjected to rinsing with ethanol, electric adjustment and sonication in a saline solution, and ion-exchange to obtain water-soluble β-glucosamine fibrin followed by nano-sized coating with immunoglobulin (γ-globulin), is used in the present film and therefore the resulting film may exhibit higher antibiotic activity and water solubility.

If necessary, 0–1 wt % of flavor, sweetener, 0–1 wt % of pigment and/or 0–1 wt % of other additives may be contained in the present film. These ingredients may be applicable to manufacturing the water-soluble film as an oral cleaning agent and, when applied to one or both sides of a biodegradable film or a conventional film, they may be applicable to manufacturing the packaging material.

The process for manufacturing the natural film of this invention will be described in detail as follows.

Firstly, the water-soluble chitosan with enhanced immunity that is a distinguishing feature of this invention, seaweeds, functional ingredients and other additives are weighed and dissolved in distilled water to obtain a gel. The concentration of the gel is adjusted to 0.001–70%. If the concentration is less than 0.001% or more than 70%, it is difficult to accomplish the desired viscosity in curing. In order to yield gel for film casting, the gel having the concentration described above is cured to the extent that its viscosity becomes 10–150 cps. If the viscosity is less than 10 cps, the formation of film is not easy; if exceeding 150 cps, the elasticity of film may be drop, so that the film is liable to be broken when film formation.

Then, the gel for film casting obtained thus is subjected to compression-molding, or is sprayed on hydrophobic polyethyleneterephthalate film or biodegradable film. The resultant is fixed by passing it through a mixed crystallization solution containing ethanol of 95–99.9 wt % and glutaraldehyde of 0.1–5 wt %. The fixed film gel is compress-molded through a film manufacturing machine and with a micro-knife, to give a film with desired size and thickness. Finally, the film is rolled and subjected to hot air drying, to obtain the water-soluble natural film of interest.

Where the natural film prepared above is used for oral cavity, it is rapidly dissolved and absorbed in oral cavity, and therefore, exhibits immediate effect. Since the natural film is processed to have a film form, it is easy to carry. In addition, where the natural film prepared above is applied to packaging a material, it can prolong the expected term of food storage because it can effectively prevent the bacteria and fungi responsible for food putrefaction.

The following specific examples are intended to be illustrative of the invention and should not be construed as limiting the scope of the invention as defined by appended claims.

PREPARATIVE EXAMPLE 1000 g of water-soluble chitosan (mean molecular weight, 100,000 to 500,000) prepared according to the process disclosed in U.S. Pat. No. 5,730,876 was decomposed with lysozyme, followed by adjusting pH to 6–7 in 30% saline. The resultant was sonicated with step adjustment for 3 hr at 45° C. and a frequency of 50–100 kHz, and allowed to stand for 2 hr at 80° C. in order to prevent alteration and modification of $NH_2$ ring, followed by ion exchange. At this time, as cationic resin, DIAION PK228 (Samyang Inc., Korea) was used at a rate of 1,500 cc/min, and as an anionic resin, the product purchased from Dupont Inc. (USA) was used at a rate of 500 cc/min. The unreacted materials and impurities found in enzymatic reaction, and residual ions were removed with carbon filter for increasing purity and integration, so that the distribution-integration efficiency of molecular weight for reliable fractionation becomes 1.1–1.9. The free ions in an aqueous phase were not found.

The distribution was integrated for isolation, and for removing residual enzyme after enzymatic treatment and fractionating macromolecule, the fractionation was carried out with respect to a series of molecular weight of 1,000,000, 600,000, 300,000, 200,000 and 100,000 in a parallel and repetitive manner. The filtration apparatus and membrane (flat membrane, width×length: 200 mm×300 mm) were manufactured in house. The pure concentrates of 70–99% was finally obtained in an objective yield of 95% (±10%).

The liquid permeated was subjected to ion-exchange more than once in order to purifying cation ($NH_2$) charge and introduce anion ($Cl^-$), so that water-soluble β-glucosamine fibrins were released. The resultant was nano-coated with 0.01–10% γ-globulin by use of 1% cholic acid preparative solution and 10% collagen as intermediate catalyst. The aqueous solution thus obtained was distilled under a room temperature, pre-cooled and freeze dried, to yield an aqueous chitosan for preparing natural film of this invention.

EXAMPLE 1

Preparation of Water-Soluble Natural Film by Compression Molding

The water-soluble gel having a concentration of 3% was prepared by using 90 wt % of chitosan prepared in Preparative Example, 5 wt % of tangle extract as seaweed, 5 wt % of astaxanthin as functional ingredient, and then cured for 24 hr at 4° C. to a viscosity of 100–110 cps (Brookfield viscometer). Thereafter, the cured gel was hardened by passing spirit-based hardening solution (mixture of 99.9 wt % ethanol and 0.1 wt % glutaraldehyde) and then the hardened gel was compress-molded with micro-knife in a film forming machinery. The molded gel was rolled and subjected to hot air drying at 80° C. and at a rate of 50 rpm, to form film. The film sample (width 3 cm, length 2 cm and thickness 0.5 mm) was prepared and used for measuring several properties.

EXAMPLE 2

Preparation of Water-Soluble Natural Film by Spray Method

The water-soluble gel having a concentration of 3% was prepared by using 50 wt % of chitosan prepared in Preparative Example, 25 wt % of *Gelidium amansii* extract as seaweed, 25 wt % of cellulose as functional ingredient, and then cured for 24 hr at 4° C. to a viscosity of 80–90 cps (Brookfield viscometer). Thereafter, the cured gel was sprayed on hydrophobic polyethyleneterephthalate film to a thickness of 0.5–0.7 mm and then hardened by passing spirit-based hardening solution (mixture of 99.9 wt % ethanol and 0.1 wt % glutaraldehyde), followed by manufacturing water-soluble natural film as Example 1. The film sample (width 5 cm, length 10 cm and thickness 0.5 mm) was prepared and used for measuring several properties.

COMPARATIVE EXAMPLE

Preparation of Natural Film Using Conventional Chitosan

Chitosan (Sigma, deacetylation of 85%) was dissolved in 1% diluted acetic acid solution to prepare a chitosan solution with a concentration of 5%. Thereafter, the film was manufactured according to a film casting method described in Example 1. Curing was performed in a hardening solution containing 99.9 wt % ethanol and 0.1 wt % glutaraldehyde) and then the hardened gel was passed through a film forming machinery, followed by hot air drying at 80° C. to finally form film. The film sample (width 3 cm, length 2 cm and thickness 0.5 mm) was prepared and used for measuring several properties. The film sample prepared in this Example was shown to have no water solubility and is considered inappropriate as an edible material due to it may damage oral mucous membrane due to its nature of strong skin irritation.

EXPERIMENTAL EXAMPLE 1

Antibiotic Activity Depending on Molecular Weight of Water Soluble Chitosan

The antibiotic activity depending on molecular weight of the water-soluble chitosans prepared in Preparative Example was measured as minimum inhibitory concentration (MIC), the results of which are summarized in Table 1.

TABLE 1

| | Type of Microorganism (MIC: $\mu$M) | | | |
|---|---|---|---|---|
| M.W.(Da) | Staphyrococcus aureus ATCC 6538P | Escherichia coli ATCC 8739 | Pseudomonas aeruginosa ATCC 9027 | Candida albicans ATCC 10231 |
| 1,000 | >600 | >600 | >600 | >600 |
| 10,000 | >600 | >600 | >600 | >600 |
| 50,000 | 300 | 300 | 300 | 300 |
| 100,000 | 5.8 | 12.8 | 19 | 19 |
| 500,000 | 11.0 | 18.7 | 21.0 | 20.0 |
| 1,000,000 | 26.0 | 27.7 | 29.3 | 28.0 |

As indicated in Table 1, the water-soluble chitosans used in preparing natural film of this invention show the potential antibiotic activity of 5.8–21.0 in a range of M.W. 100,000–500,000.

EXPERIMENTAL EXAMPLE 2

Antibiotic Activity Depending on Concentration of Water Soluble Chitosan

The concentration-dependent antibiotic activity of the water-soluble chitosans prepared in Preparative Example was measured, the results of which are summarized in Table 2.

TABLE 2

| Conc. of chitosan gel | MIC ($\mu$M) |
|---|---|
| 1% | 9 |
| 2% | 7 |

The antifungal activity to *Candida albicans* generally known to cause stomatitis, thrush and dental caries in oral cavity was measured as minimum inhibitory concentration.

As described in Table 2, the water-soluble chitosan gels show concentration-dependent antifungal activity, demonstrating that the water-soluble chitosan gel can prevent the attachment of *Candida albicans* to human oral-derived cells and exhibit antifungal activity.

EXPERIMENTAL EXAMPLE 3

Antibiotic Activity of Water Soluble Chitosan Film

The antibiotic activity of the water-soluble chitosan films prepared in Examples 1 and 2 was tested with regard to 4 types of gram-negative bacteria as follows:

The antibiotic activity was measured by counting the number of colonies generated on an agar plate. 0.5 ml of cultured bacteria, 0.5 ml of the autoclaved composition for preparing the film of this invention and 0.05 M acetate buffer (pH 6.0) were mixed and incubated with agitation for 1 hr at 37° C.

For preparing control group, 4.5 ml of acetate buffer solution were employed instead of the composition for preparing the film of this invention. 1 ml of the mixed solution was diluted 10-fold.

The experimental and control groups with tryptic soy agar medium (TSA, Difco) were dispensed to plastic Petri dishes and incubated for 24 hr in a 37° C. incubator. The formed colonies were counted and then the antibiotic activity was calculated according to the following mathematical formula. The results are found in Table 3.

Antibiotic Activity (%)=[(the number of colony in control group−the number of colony in experimental group)/the number of colony in control group]×100

TABLE 3

| Types of Bacteria (gram- | Antibiotic activity (%)* | | |
|---|---|---|---|
| negative Bacteria) | Exam. 1 | Exam. 2 | Control |
| *Escherichia coli* | >99 ± 0 | >99 ± 0 | <12 ± 0 |
| *Escherichia coli* O-157 | >99 ± 0 | >99 ± 0 | <12 ± 0 |
| *Salmonella typhi* | >99 ± 0 | >99 ± 0 | <12 ± 0 |
| *Pseudomonas aeruginosa* | >68 ± 3 | >68 ± 0 | <9 ± 2 |

*mean ± standard deviation

The microorganisms used in measurement of antibiotic activity of chitosans prepared according to the present method were dispensed from KCTC (Korean Collection forf Type Cultures) and ATCC (American Type Culture Collection), including *Escherichia coli, Escherichia coli O-157, Salmonella typhi* and *Pseudomonas aeruginosa.*

*E. coli* is a bacteria having typical characteristics of gram-negative bacteria, serving as indicator demonstrating contamination of pathogenic microorganisms in examining water quality. Therefore, the prevention of *E. coli* growth enables to reduce the contamination level of harmful pathogenic microorganisms. In particular, *E. coli* O157 having typical characteristics of gram-negative bacteria causes enterorrhagia on infecting to human body. Furthermore, *Salmonella typhi* is a gram-negative bacterium and the prevention of its growth results in the prevention of hematosepsis and gastroenteritis. *Pseudomonas aeruginosa* is otitismedia-causing bacterium and the prevention of its growth is thus responsible for the prevention of inflammation induction.

Consequently, as shown in Table 3, it can be verified that the water-soluble chitosans prepared in Examples 1 and 2 exhibit superior prevention effect, i.e., antibiotic activity to bacteria described above to conventional chitosan.

EXPERIMENTAL EXAMPLE 4

Minimum Inhibitory Concentration of Water Soluble Chitosan Film

Bacteria were inoculated into 5 ml of tryptic soy broth (TSB) containing 1 ml of water-soluble chitosan film composition prepared in Examples and 1 and 2 or 1 ml of conventional chitosan film composition prepared in Comparative Example, followed by incubating for 18 hr at 37° C. Then, the minimum inhibitory concentration was measured and shown in FIG. 1.

The minimum inhibitory concentration (MIC) refers to a minimum concentration of sample tested at cell growth point showing unobservable growth pattern under naked eye or microscope.

The minimum inhibitory concentration of water-soluble chitosan film composition prepared according to this invention show less than 0.06% with respect to gram-negative bacteria except for *Pseudomonas aeruginosa* (0.25%). Compared to the result of control group (32%), these results described above are shown to have excellent minimum inhibitory concentration and therefore, it can be appreciated that the water-soluble chitosan film composition of this invention exhibit much higher antibiotic activity even at a very low concentration.

EXPERIMENTAL EXAMPLE 5

Figure 2:
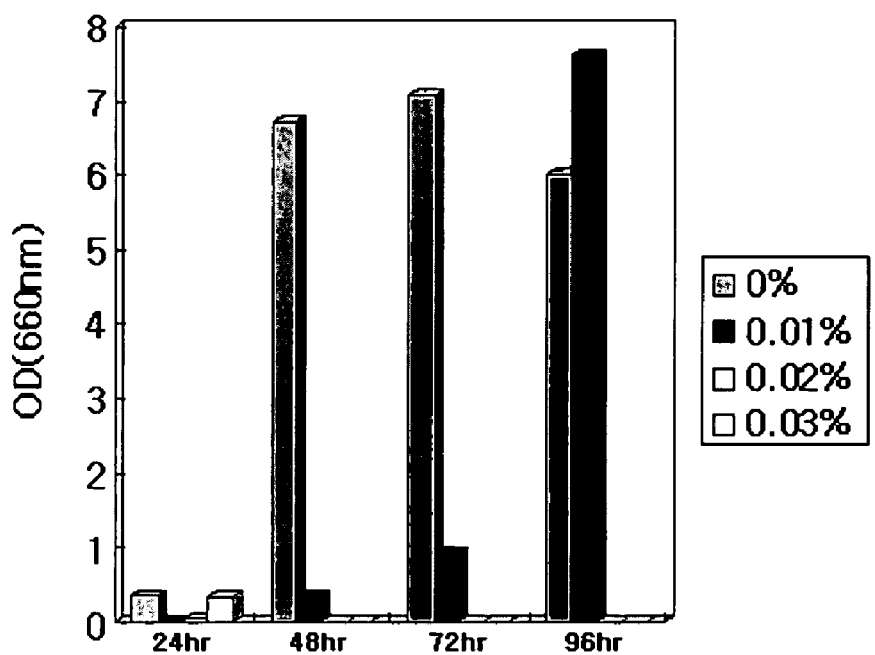
FIG. 2 is a graph showing the prevention effects to *E. coli* depending on concentration of chitosan used in the present natural film.
Figure 3:
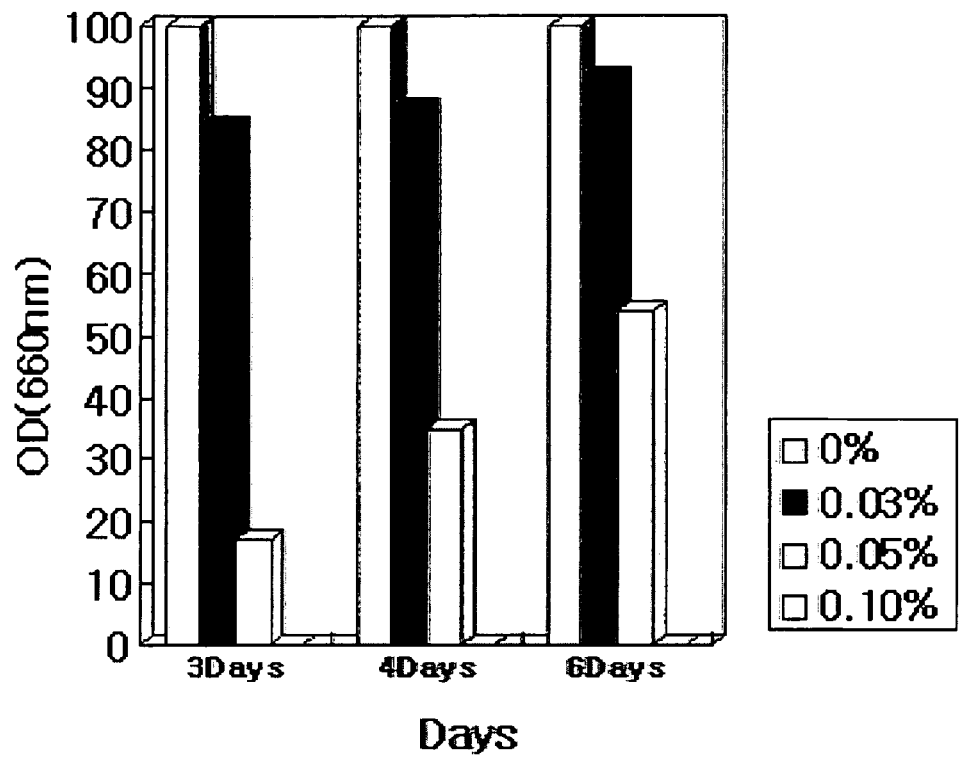
FIG. 3 is a graph representing the prevention effects to *Fusarium solani* depending on concentration of chitosan used in the present natural film.
Figure 4:
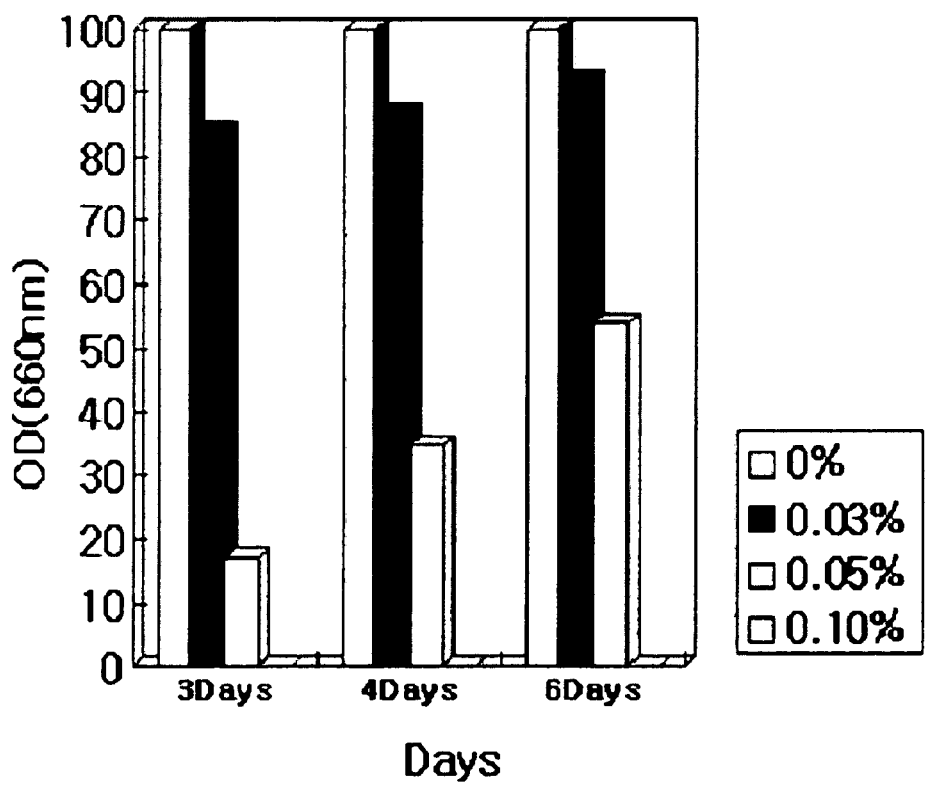
FIG. 4 is a graph representing the prevention effects to *Lactobacillus casei* depending on concentration of chitosan used in the present natural film.

Antibiotic Activity Depending on Concentration of Water Soluble Chitosan Film Composition The growth prevention effect of the water-soluble chitosan film composition of this invention was examined with respect to *E. coli, Fusarium solani* and *Lactobacillus casei*. The prevention effect was evaluated by measuring turbidity of medium at specific time intervals with spectrophotometer (660 nm). The results are shown in FIGS. 2, 3 and 4.

As described above, the water-soluble natural film according to the present invention, unlike the conventional film containing chitosan, exhibits water solubility, so that the antibiotic activity of water-soluble chitosan is applicable to more various fields, and seaweeds and functional ingredients contained therein improve miscibility with chitosan and impart elasticity to matrix of a film to enable film molding with convenience. In addition, since the natural film of this invention comprise natural materials as active ingredients, it shows more compatibility to human body and elicits more favorable feeling when taken in. In particular, the film composition itself is processed to form a film with a desired thickness and size and is coated on conventional biodegradable resin film.

Since the final product as a film is easy to carry and take in and is successful in the prevention of the growth of oral bacteria and the removal of halitosis, it is very desirable to use it I preparing an oral cleaning agent of film type with immediate effect.

In addition, where the natural film of this invention manufactured by coating conventional film at a concentration of 100–500 ppm is applied to a packaging material, it is successful in preventing the growth of harmful microorganisms responsible for putrefaction of food owing to its excellent antibiotic activity, so that it is possible to freshly store food for a long period of time. Additionally, owing to its good biodegradability, the film is used as a biodegradable packaging material.

What is claimed is:

1. A water-soluble natural film composition containing chitosan, which comprises:
    (a) 20–99.98 wt % of water-soluble chitosan with enhanced immunity prepared in such a manner that chitin/chitosan decomposed with lysozyme is sonicated in a saline solution and is subjected to ion-exchange to obtain water-soluble β-glucosamine fibrin followed by nanocoating said β-glucosamine fibrin with γ-globulin as an immune protein;
    (b) 0.01–75 wt % of at least one seaweeds selected from the group consisting of *Gelidium amansii*, jellyfish, brown seaweed, tangle and their extracts; and
    (c) 0.01–30 wt % of at least one functional ingredients selected from the group consisting of γ-globulin, cholic acid, astaxanthin, rutin, lecithin, *Inula helenium* L., cellulose and collagen.

2. The composition according to claim 1, wherein said water-soluble chitosan has a molecular weight of 10,000 to 1,000,000 Da.

3. A method for preparing water-soluble natural film containing chitosan, which comprises the steps of:
    (a) preparing water-soluble chitosan with enhanced immunity prepared in such a manner that chitin/chitosan decomposed with lysozyme is sonicated in a saline solution and is subjected to ion-exchange to obtain water-soluble β-glucosamine fibrin followed by nanocoating said β-glucosamine fibrin with γ-globulin as an immune protein;
    (b) preparing a gel with a concentration of 0.001 to 70% by dissolving in distilled water 20–99.98 wt % of said water-soluble chitosan with enhanced immunity; 0.01–75 wt % of at least one seaweeds selected from the group consisting of *Gelidium amansii*, jellyfish, brown seaweed, tangle and their extracts; and 0.01–30 wt % of at least one functional ingredients selected from the group consisting of γ-globulin, cholic acid, astaxanthin, rutin, lecithin, *Inula helenium* L., cellulose and collagen;
    (c) curing said gel prepared in the step of (b), whereby said gel shows a viscosity of 10 to 150 cps;
    (d) hardening said gel cured in the step of (c) with ethanol of 95–99.9 wt % and glutaraldehyde of 0.1–5 wt %; and
    (e) compression-molding said hardened gel in the step of (d) or spraying said hardened gel on one side or both sides of biodegradable film or conventional film, followed by drying.

4. A water-soluble natural film containing chitosan used as an oral cleaning agent, wherein said film is formed from the composition of claim 1.

5. A water-soluble natural film containing chitosan for packaging material with antibiotic potential, wherein said packaging material is prepared by coating one side or both sides of a biodegradable film or conventional film with the water-soluble natural film composition of claim 1.

* * * * *